United States Patent [19]

Adams et al.

[11] 4,212,997

[45] Jul. 15, 1980

[54] PROCESS FOR RECOVERING 2,2-BIS(4-HYDROXYPHENYL)PROPANE FROM AN ADDUCT OF 2,2-BIS(4-HYDROXYPHENYL)PROPANE AND PHENOL

[75] Inventors: John N. Adams, Pittsburgh, Pa.; Gaylord M. Kissinger, Mt. Vernon, Ind.; Michael C. Lee, Pensacola, Fla.

[73] Assignee: General Electric Company, Pittsfield, Mass.

[21] Appl. No.: 919,667

[22] Filed: Jun. 27, 1978

[51] Int. Cl.$^2$ .............................................. C07C 37/44
[52] U.S. Cl. ................................... 568/724; 568/728
[58] Field of Search .............................. 568/724, 728

[56] References Cited

U.S. PATENT DOCUMENTS

| | | | |
|---|---|---|---|
| 2,791,616 | 5/1957 | Luten | 260/619 |
| 2,845,464 | 7/1958 | Luten | 568/724 |
| 2,959,622 | 11/1960 | Gimme et al. | 568/724 |
| 3,073,868 | 1/1963 | Buffalo et al. | 260/619 |
| 3,111,544 | 11/1963 | Jonis et al. | 568/724 |
| 3,162,690 | 12/1964 | Marx | 260/619 |
| 3,277,183 | 10/1966 | Heller et al. | 260/619 |
| 3,290,391 | 12/1966 | Buffalo et al. | 260/619 |
| 3,326,986 | 6/1967 | Dugan et al. | 260/619 A |
| 3,359,281 | 12/1967 | Schlichting et al. | 368/724 |
| 3,535,389 | 10/1970 | DeJong | 260/619 |
| 3,627,846 | 12/1971 | Meyer | 568/724 |
| 3,673,262 | 6/1972 | Prahl et al. | 260/619 |
| 3,919,330 | 11/1975 | Kwantes et al. | 260/619 |
| 3,936,507 | 2/1976 | Ligorati et al. | 568/724 |
| 3,972,950 | 8/1976 | Kwantes | 260/619 |

FOREIGN PATENT DOCUMENTS

| | | |
|---|---|---|
| 147105 | 1/1973 | Czechoslovakia . |
| 971013 | 11/1958 | Fed. Rep. of Germany . |
| 1294664 | 7/1970 | Fed. Rep. of Germany . |
| 1580676 | 7/1969 | France . |
| 45-22539 | 7/1970 | Japan . |
| 45-39251 | 12/1970 | Japan . |
| 48-30269 | 9/1973 | Japan . |
| 57925 | 8/1969 | Poland . |
| 902350 | 8/1962 | United Kingdom ................ 568/724 |
| 1149322 | 4/1969 | United Kingdom ................ 260/619 |

OTHER PUBLICATIONS

Boroviska et al., "C.A.", 60:2832d, (1963).
Levkovich et al., "C.A.", 55:11370h, (1960).
Matsukane, "C.A." 66:38331j (1967).
Hirt et al., "C.A.", 67:53879h (1967).

*Primary Examiner*—Norman Morgenstern
*Attorney, Agent, or Firm*—Morgan, Finnegan, Pine, Foley & Lee

[57] ABSTRACT

The compound 2,2-bis(4-hydroxyphenyl)propane is recovered in the form of rhombic crystals from an essentially non-crystalline mixture comprising 2,2-bis(4-hydroxyphenyl)propane, organic by-products of the condensation reaction of phenol and acetone, and phenol by lowering the temperature of the mixture from an elevated state to a temperature which is low enough to cause the separation of the phenol and 2,2-bis(4-hydroxyphenyl)propane in equimolar proportions as a crystalline adduct, recovering the adduct, forming a mixture of the adduct and water at an elevated temperature sufficient to completely melt the adduct, and thereafter lowering the temperature of the mixture of water and melted adduct to cause the separation of the 2,2-bis(4-hydroxyphenyl)propane in the form of rhombic crystals substantially free of the phenol. The crystals are easily handled and recovered by means such as filtration or centrifugation, and they can be formed into high quality polycarbonate molding resins.

11 Claims, No Drawings

PROCESS FOR RECOVERING 2,2-BIS(4-HYDROXYPHENYL)PROPANE FROM AN ADDUCT OF 2,2-BIS(4-HYDROXYPHENYL)PROPANE AND PHENOL

This invention relates to a process for the recovery of 2,2-bis(4-hydroxyphenyl)propane, also known as bisphenol-A, substantially in the form of easy-to-handle rhombic crystals from a mixture resulting from the condensation reaction of phenol and acetone. The process involves isolating an adduct of bisphenol-A and phenol from the reaction mixture, and treating the adduct using a unique combination of process steps and conditions to cause the selective separation of only the bisphenol-A portion of the adduct in the desired crystalline form.

BACKGROUND OF THE INVENTION

The compound 2,2-bis(4-hydroxyphenyl)propane, also known as bisphenol-A, enjoys major use as a co-reactant for phosgene in the production of aromatic polycarbonate resins suitable for molding applications. It is known that 2,2-bis(4-hydroxyphenyl)propane can be prepared by the acid-catalyzed reaction of acetone with a substantial excess of phenol. Upon completion of the reaction and after the removal of the acid catalyst and by-product water, a mixture comprising bisphenol-A, unreacted phenol and organic by-products of the condensation reaction results.

Various methods for recovering the bisphenol-A from its reaction mixture have been proposed in the art. Dugan et al, U.S. Pat. No. 3,326,986, discloses a procedure wherein "crude" bisphenol-A is separated from its reaction mixture by precipitation or distillation, the "crude" bisphenol-A is melted in the presence of water, and the melt is thereafter crystallized to obtain the bisphenol-A in purer form.

Luten, U.S. Pat. No. 2,791,616, discloses a process for recovering bisphenol-A from a phenol-rich reaction mixture wherein the bisphenol-A and phenol are separated in equimolar proportions in the form of a crystalline adduct, the adduct is thereafter treated to selectively melt only the phenol portion, and the bisphenol-A remaining in solid crystalline form is collected.

Also of interest are Keller et al, U.S. Pat. No. 2,777,183, who uses an alkaline substance to partially neutralize the bisphenol compound during purification; French Pat. No. 1,580,676, which discloses purifying bisphenols by repeated washings with warm water; Boroviska et al, Chem, Abstracts 60:2832(c), which uses even hotter water to purify bisphenols; German Pat. No. 971,013 (1954), which also involves neutralization with base in the purification of bisphenols; Czech Pat. No. 147,105 (1973), which describes countercurrent extraction processes for the purification of bisphenols; Japanese Pat. No. 30269/73, which uses an emulsion of an organic solvent, surfactant and water to purify bisphenol; Japanese Patent Publication No. SHO-45-39251 which discloses distilling an adduct of bisphenol and phenol in the presence of a high melting glycol; Japanese Patent Publication No. SHO-45-22539 which discloses distilling an adduct of bisphenol and phenol in the presence of an aliphatic dicarboxylic acid ester; De-Jong, U.S. Pat. No. 3,535,389, who mixes the impure bisphenol with a water-organic solvent mixture and steams out the solvent; Polish Pat. No. 57,925 describes melting bisphenols in water, acid and salt, and then crystallizing; Levkovich et al, Chemical Abstracts Vol. 55:11370h who free bisphenols of impurities by washing with dilute ammonium hydroxide; and Marx et al, U.S. Pat. No. 3,162,690 who form adducts of bisphenols with cresols, then decompose them for purification.

There has now been discovered a new and very simple process for recovering bisphenol-A from a reaction mixture resulting from the condensation of acetone and excess phenol, wherein the bisphenol-A is cleanly separated from a melt of both the phenol and the bisphenol-A in the form of highly desirable, easy-to-handle rhombic crystals, without the need to use high temperatures, liquid-liquid extraction, extraction with water containing surfactants, or sodium chloride, or acid, or alkali or ammonium hydroxide, etc.

DESCRIPTION OF THE INVENTION

This invention, in its broadest aspects, comprises a process for recovering 2,2-bis(4-hydroxyphenyl)propane in the form of rhombic crystals from a non-crystalline mixture, the reaction mixture comprising 2,2-bis(4-hydroxyphenyl)propane, organic by-products resulting from the condensation reaction of phenol and acetone, and phenol, wherein said phenol is present in at least an equimolar amount with respect to said 2,2-bis(4-hydroxyphenyl)propane, the process comprising:

(a) lowering the temperature of the mixture from an elevated temperature at which the 2,2-bis(4-hydroxyphenyl)propane is soluble to a temperature sufficient to cause the separation from the mixture of the 2,2-bis(4-hydroxyphenyl)propane and phenol in equimolar proportions as a crystalline adduct and recovering the adduct;

(b) forming an admixture of the adduct of step (a) with an excess of water at an elevated temperature which is at least sufficient to completely melt the adduct, the water being present in an amount at least sufficient to retain the phenol portion of the adduct upon subsequent separation of the 2,2-bis(4-hydroxyphenyl)propane from the mixture;

(c) lowering the temperature of the mixture of water and melted adduct to a temperature sufficient to cause the selective separation of the 2,2-bis(4-hydroxyphenyl)propane portion of the adduct in the form of rhombic crystals substantially free of said phenol portion; and (d) recovering the rhombic crystals of 2,2-bis(4-hydroxyphenyl)propane.

In preferred embodiments, the process of this invention also includes the step of (e) contacting the recovered rhombic crystals of 2,2-bis(4-hydroxyphenyl)propane with liquid(s) selected from among water and/or organic hydrocarbons in which the 2,2-bis(4-hydroxyphenyl)propane is insoluble or only slightly soluble, to remove adsorbed water soluble and/or organic solvent soluble impurities from the crystals.

By way of illustration, an essentially non-crystalline reaction mixture resulting from the conventional acid-catalyzed condensation reaction of acetone with an excess of phenol, still at an elevated temperature which is sufficient to maintain the desired product, 2,2-bis(4-hydroxyphenyl)propane, in solution is adjusted to less than about 45° C., preferably from about 38° to about 42° C., whereupon a non-rhombic crystalline adduct of 2,2-bis(4-hydroxyphenyl)propane and phenol, in equimolar proportions, precipitates. The crystalline adduct is then recovered conventionally by means such as filtration, centrifugation, or the like. Centrifugation is preferred as providing a somewhat better separation of the adduct from its mother liquor. Another preferred procedure comprises filtration followed by centrifugation of the filtered adduct.

After recovery, the adduct is preferably washed or rinsed with suitable quantities of phenol to remove any adsorbed phenol-soluble impurities such as color bodies, organic by-products of the condensation reaction, and the like. Preferably, an amount of phenol of about 0.5 part by weight of phenol per part by weight of adduct is employed, but larger or smaller amounts can be used as desired.

The crystalline adduct is then admixed with water to form an aqueous slurry, and mixing is continued at a temperature sufficient to cause the adduct to melt completely. The minimum preferred temperature for this purpose is about 80° C., and preferably from about 80° to about 90° C. In carrying out this procedure, in general, an amount of water sufficient to provide a weight ratio of water to adduct of from about 8:1 to about 10:1, or a weight ratio of water to the phenol portion of the adduct of from about 25:1 to about 31:1, is used. Especially preferably, a weight ratio of water to adduct of 10:1 is employed.

After the adduct is completely melted, the temperature of the mixture of water and melted adduct is gradually lowered, preferably to a temperature in the range of from about 45° to about 50° C., whereupon the 2,2-bis(4-hydroxyphenyl)propane portion of the adduct only selectively crystallizes in the shape of rhomboids, and substantially without co-precipitation of the phenol portion of the adduct. The rhombic crystals are recovered by filtration, centrifugation, or the like.

If desired, the recovered crystals can be washed with water and/or an organic solvent such as a halohydrocarbon, e.g., methylene chloride, or the like, to further purify the crystalline end product. In a preferred procedure, the crystals of 2,2-bis(4-hydroxyphenyl)propane are washed with water in the amount of about 0.5 part by weight of water per part by weight of the crystals, followed by a methylene chloride wash using about 1.5 parts by weight of methylene chloride per part by weight of the crystals.

DESCRIPTION OF THE SPECIFIC EMBODIMENTS

The process of this invention is illustrated in the following examples. These are not intended to be limiting, however.

In each of the examples, the starting mixture comprising bisphenol-A, by-products from the condensation reaction of phenol and acetone, and phenol is obtained upon completion of a conventional acid-catalyzed reaction between acetone and phenol, and removal therefrom by distillation of the acid catalyst and water of reaction. The phenol in the starting mixture in each of the following examples is present in an amount exceeding a molecular equivalent of the bisphenol-A. Adduct formation in each of the examples is accomplished under a nitrogen atmosphere. All analyses are normalized to 100%.

EXAMPLE 1

Four thousand, eight hundred and ninety-five grams of a mixture comprising 60.5% by weight of phenol, 34.1% by weight of bisphenol-A and 5.4% by weight of by-products are cooled to 40° C. to precipitate an equimolar adduct of bisphenol-A and phenol. The adduct and its mother liquor are centrifuged to remove the mother liquor, and the adduct is washed with 1,000 grams of phenol at a temperature of 50° C. Analysis of the adduct indicates a composition as follows:

| Ingredients | Amount, % By Weight |
|---|---|
| bisphenol-A | 64.7 |
| phenol | 34.1 |
| by-products | 1.2 |

Thereafter, a 12-liter flask equipped with a stirrer, condenser and thermometer is charged with 8,200 milliliters (ml) of distilled water. The water is heated to 88° C., and 800 grams of washed adduct is added, whereupon the adduct melts. The mixture of water and adduct is stirred for about 15 minutes, and then allowed to cool to 50° C. over a period of about 1¾ to 2 hours. Crystallization within the mixture begins at about 70° C. Separation of the crystals is accomplished by centrifugation at 50° C., and the crystals are washed with 250 ml of water at 50° C., to yield rhombic crystals of bisphenol-A which are substantially free of phenol.

EXAMPLE 2

Four thousand, five hundred and forty-six grams of a mixture comprising 59.9% by weight of phenol, 34.3% by weight of bisphenol-A and 5.8% by weight of by-products is cooled to 40° C. to precipitate an essentially equimolar adduct of bisphenol-A and phenol. Analysis to the adduct indicates a composition as follows:

| Ingredients | Amount, % By Weight |
|---|---|
| bisphenol-A | 65.1 |
| phenol | 33.6 |
| by-products | 1.2 |

The adduct is separated from its mother liquor by centrifugation and washed with 900 grams of phenol at 50° C.

Thereafter, a 12-liter flask equipped with a stirrer, condenser and thermometer is charged with 7,787 ml of distilled water. The water is heated to 90° C., 800 grams of washed adduct is added, and the temperature is maintained at 85° C. for about 15 minutes, with continuous stirring. The mixture is then allowed to cool to 50° C., with stirring continued, and initial crystal formation is observed to begin at 72° C. The crystals are separated by centrifugation and washed in the centrifuge with 250 ml of water at 50° C., to yield rhombic crystals of bisphenol-A.

In like manner, other mixtures comprising phenol, bisphenol-A and by-products are treated according to this invention. The results are summarized as follows:

ADDUCT CRYSTALLIZATION

Typical compositions of the starting mixtures are shown in Table I. The mixtures are cooled to 40°–45° C. to effect formation of the respective adducts.

TABLE I

| Ingredients | Mixture Composition, % By Weight | Adduct Composition, % By Weight |
|---|---|---|
| Bisphenol-A | 30–35 | 63–65 |
| Phenol | 55–62 | 30–34 |

TABLE I-continued

| Ingredients | Mixture Composition, % By Weight | Adduct Composition, % By Weight |
|---|---|---|
| By-products | 3.5–5.5 | 0.5–1.5 |

BISPHENOL-A CRYSTALLIZATION

After separation from its mother liquor, the adduct is washed with phenol and then mixed with water at a temperature sufficient to yield a liquor wherein the adduct is melted. Table II shows the average yield and quality of the bisphenol-A and product at various temperatures at which the adduct is melted, using a weight ratio of water to the phenol portion of the adduct of 26:1. As is shown, when the temperature is increased above 80° C. there is no advantage, since the yield of bisphenol-A tends to decrease.

TABLE II

| Melt Temperature | Bisphenol-A Yield* | % Phenol in Bisphenol-A |
|---|---|---|
| 100° C. | 83% | 0.84 |
| 80° C. | 84.5% | 1.3 |

*Adduct washed with phenol; bisphenol-A crystals unwashed

The amount of water employed in melting the adduct should be of a quantity sufficient to retain the phenol portion of the adduct upon subsequent crystallization therefrom of the bisphenol-A portion. Table III compares the average quality of the bisphenol-A end product with various quantities of water employed, reported as a ratio of the weight of water to the weight of the phenol portion of the adduct. As is shown in Table III a ratio of 25:1 is satisfactory, but 18:1 left too much phenol in the product.

TABLE III

| Weight Ratio Water/Phenol | Bisphenol-A Quality* % Phenol | APHA Value** |
|---|---|---|
| 31:1 | ND | 27 |
| 25:1 | ND | 50 |
| 18:1 | 1.8 | 68 |

ND None detected by gas chromatography
*Final product quality (adduct washed with phenol; bisphenol-A crystals washed with water and methylene chloride)
**According to American Public Health Association standards; lower values indicate presence of lesser amounts of color bodies (impurities).

Rhombic crystallization of bisphenol-A from the liquor wherein the adduct is melted is accomplished by cooling this liquor to a temperature which causes crystalline precipitation of the bisphenol-A substantially without co-precipitation of the phenol. The crystals of bisphenol-A are then physically recovered by filtration or centrifugation. Table IV shows average yield and quality of bisphenol-A recovered at various crystallization temperatures. As is shown in Table IV, temperatures in the range of from about 45°–50° C. are preferable. At higher temperatures the yield of bisphenol-A decreases, while at lower temperatures co-precipitation of phenol increases.

TABLE IV

| Effect of Crystallization Temperature | | |
|---|---|---|
| Crystallization Temperature | % Phenol in Bisphenol-A | Bisphenol-A* Yield |
| 55° | 1.3 | 84.5 |
| 50° | 0.6 | 93.8 |
| 45° | 0.7 | 89.9 |
| 40° | 2.5 | 91.8 |
| 35° | 4.1 | 89.1 |

*Adduct washed with phenol, bisphenol-A-crystals unwashed.

Table V summarizes average final bisphenol-A product quality obtained with processes according to this invention. These are shown as recovered directly upon crystallization, without washing by water or solvent.

TABLE V

| | Bisphenol-A Product* |
|---|---|
| Bisphenol-A | 98–99.5% |
| Phenol | 0–1% |
| By-products | 2000 ppm[1] |

*Adduct washed with phenol; bisphenol-A crystals unwashed
[1] Only the o,p'-isomer of bisphenol-A

EXAMPLE 3

Five hundred and fifty grams of a mixture comprising 56.8% by weight of phenol, 37.3% by weight of bisphenol-A and 5.9% by weight of by-products is cooled to 40° C. to precipitate an equimolar adduct of bisphenol-A and phenol. The mother liquor is removed from the adduct on a Buchner funnel and the adduct is washed twice with 100 and 62 grams of phenol at a temperature of 42° C. Analysis of the adduct by liquid chromatography indicates a composition as follows:

| Ingredients | Amount, % by Weight |
|---|---|
| Bisphenol-A | 62.3 |
| Phenol | 37.2 |
| By-products | 0.5 |

Thereafter, a five-liter flask equipped with a stirrer, condenser and thermometer is charged with 2500 ml of distilled water. The water is heated to 100° C. and 260 grams of washed adduct is added, whereupon the adduct melts. The mixture of water and adduct is stirred for about 10 minutes and then allowed to cool to 50° C. over a period of about four to five hours with continuous stirring. Initial crystal formation is observed to begin at about 70° C. The crystals are separated from the mother liquor with a Buchner funnel and washed three times with 250 ml, 100 ml and 100 ml of an organic solvent, such as methylene chloride or benzene, to yield rhombic crystals of bisphenol-A.

Obviously, other modifications and variations of the present invention are possible in light of the above teachings. It is, therefore, to be understood that changes may be made in the particular embodiments of the invention described which are within the full intended scope of the invention as defined in the appended claims.

We claim:
1. A process for recovering 2,2-bis(4-hydroxyphenyl)propane in the form of rhombic crystals from a non-crystalline mixture at an elevated temperature above room temperature, the reaction mixture comprising 2,2-bis(4-hydroxyphenyl)propane, organic by-products resulting from the condensation reaction of phenol and acetone, and phenol, wherein said phenol is present in at least an equimolar amount with respect to said 2,2-bis(4-hydroxyphenyl)propane, the process comprising:
(a) lowering the temperature of said mixture from an elevated temperature at which the 2,2-bis(4-hydroxyphenyl)propane is soluble to a temperature sufficient to cause the separation from said mixture of said 2,2-bis(4-hydroxyphenyl) propane and phenol in equimolar proportions as a crystalline adduct and recovering the adduct;
(b) forming an admixture of said adduct of step (a) with an excess of water at an elevated temperature which is at least sufficient to completely melt the adduct, the water being present in an amount at least sufficient to retain the phenol portion of the adduct upon subsequent crystallization therefrom of the 2,2-bis(4-hydroxyphenyl)propane;
(c) lowering the temperature of said mixture of water and melted adduct to a temperature sufficient to cause the selective separation therefrom of the 2,2-bis(4-hydroxyphenol)propane portion of the adduct in the form of rhombic crystals substantially free of said phenol portion; and
(d) recovering said rhombic crystals of 2,2-bis(4-hydroxyphenyl)propane.

2. A process as defined in claim 1 which further comprises:
(e) contacting the recovered rhombic crystals of 2,2-bis(4-hydroxyphenyl)propane with a liquid selected from among water, organic hydrocarbons or mixtures thereof in which said 2,2-bis(4-hydroxyphenyl)propane is insoluble or only slightly soluble, to remove adsorbed water soluble and/or organic solvent soluble impurities therefrom.

3. A process as defined in claim 1 wherein in step (a) the temperature of said non-crystalline mixture comprising 2,2-bis(4-hydroxyphenyl)propane, organic by-products and a phenol is lowered to less than about 45° C.

4. A process as defined in claim 3 wherein in step (a) the temperature is lowered to a value in the range of from about 38° to about 42° C.

5. A process as defined in claim 1 wherein in step (b) the weight ratio of water to the phenol portion of said adduct is in the range of from about 25:1 to about 31:1.

6. A process as defined in claim 1 wherein step (b) is conducted at a temperature in the range of from about 80° to about 90° C.

7. A process as defined in claim 1 wherein in step (c) the temperature of said mixture of water and melted adduct is lowered to a temperature in the range of from about 45° to about 50° C.

8. A process as defined in claim 1 wherein the recovered adduct of step (a) is contacted with phenol to remove adsorbed impurities prior to treatment with step (b).

9. A process as defined in claim 2 wherein the organic hydrocarbon is a halohydrocarbon.

10. A process as defined in claim 9 wherein the halohydrocarbon is methylene chloride.

11. A process for recovering 2,2-bis(4-hydroxyphenyl)propane in the form of rhombic crystals from a non-crystalline mixture at an elevated temperature above room temperature, the reaction mixture comprising 2,2-bis(4-hydroxyphenyl)propane, organic by-products resulting from the condensation reaction of phenol and acetone, and phenol, wherein said phenol is present in at least an equimolar amount with respect to said 2,2-bis(4-hydroxyphenyl)propane, the process comprising:
(a) lowering the temperature of said mixture from an elevated temperature at which the 2,2-bis(4-hydroxyphenyl)propane is soluble to a temperature in the range of from about 38° to about 42° C. and sufficient to cause the separation from said mixture of said 2,2-bis(4-hydroxyphenyl)propane and phenol in equimolar proportions as a crystalline adduct and recovering the adduct;
(b) forming an admixture of said adduct of step (a) with an excess of water at an elevated temperature in the range of from about 80° to about 90° C. and which is at least sufficient to completely melt the adduct, the water being present in an amount of from about 25:1 to about 31:1 with respect to the phenol portion of the adduct and at least sufficient to retain the phenol portion of the adduct upon subsequent crystallization therefrom of the 2,2-bis(4-hydroxyphenyl)propane;
(c) lowering the temperature of said mixture of water and melted adduct to a temperature in the range of from about 45° to about 50° C. and sufficient to cause the selective separation therefrom of the 2,2-bis(4-hydroxyphenyl)propane portion of the adduct in the form of rhombic crystals substantially free of said phenol portion; and
(d) recovering said rhombic crystals of 2,2-bis(4-hydroxyphenyl)propane.

* * * * *